(12) United States Patent
Kim et al.

(10) Patent No.: US 8,846,789 B2
(45) Date of Patent: Sep. 30, 2014

(54) PHOSPHONATE BASED COMPOUND AND FLAME RETARDANT STYRENIC RESIN COMPOSITION INCLUDING THE SAME

(75) Inventors: Woo Joong Kim, Anyang-si (KR); Man Suk Kim, Seongnam-si (KR); Beom Jun Joo, Seoul-si (KR); Seon Ae Lee, Seoul-si (KR); Byun Kun Lee, Gunpo-si (KR)

(73) Assignee: Cheil Industries Inc., Gumi-si (KR)

( * ) Notice: Subject to any disclaimer, the term of this patent is extended or adjusted under 35 U.S.C. 154(b) by 470 days.

(21) Appl. No.: 13/166,203

(22) Filed: Jun. 22, 2011

(65) Prior Publication Data

US 2011/0263765 A1  Oct. 27, 2011

Related U.S. Application Data

(63) Continuation-in-part of application No. PCT/KR2009/007631, filed on Dec. 21, 2009.

(30) Foreign Application Priority Data

Dec. 29, 2008 (KR) .................. 10-2008-0135866
Oct. 30, 2009 (KR) .................. 10-2009-0104023

(51) Int. Cl.
*C08K 5/5357* (2006.01)
*C07F 9/6571* (2006.01)
*C07F 9/12* (2006.01)
*C08K 5/5313* (2006.01)

(52) U.S. Cl.
CPC ......... *C07F 9/657181* (2013.01); *C08K 5/5357* (2013.01); *C07F 9/12* (2013.01); *C08K 5/5313* (2013.01)
USPC ........................................... 524/117; 558/83

(58) Field of Classification Search
USPC ......................................................... 524/117
See application file for complete search history.

(56) References Cited

U.S. PATENT DOCUMENTS

2010/0010128 A1  1/2010  Levchik et al.
2010/0234495 A1  9/2010  Roth

FOREIGN PATENT DOCUMENTS

WO   2007-081904 A1   7/2007
WO   2008-119693 A1   10/2008
WO   2010/076995 A2   7/2010

OTHER PUBLICATIONS

International Search Report in counterpart International Application No. PCT/KR2009/007631 dated Jul. 23, 2010, pp. 1-2.
Haranath et al., "Syntheses and Antimicrobial Activity of Some Novel 6-Substituted Dibenzp[d,f][1,3,2] dioxaphosphenpin-6-oxides, Sulfides, and Selenides", Synthetic Communications, vol. 37, pp. 1697-1708 (2007).
Kasthuraiah et al., "Syntheses, Spectral Property, and Antimicrobial Activities of 6-a-amino dibenzo[d,f][1,3,2] dioxaphosphenpin 6-oxides", Heteroatom Chemistry, vol. 18, No. 1, pp. 2-8 (2007).
Alyssa, et al., "The Conformation of Medium-Sized Heterocycles: Synthesis and Solid-State Conformation of a 6-Arylthio-Substituted Dibenzo-[d,f] [1,3,2]Dioxaphosphepin", Phosphorus, Sulfur, and Silicon and the Related Elements, vol. 82, Issue 1-4, Abstract, pp. 1-2 (1989).

*Primary Examiner* — Doris Lee
(74) *Attorney, Agent, or Firm* — Additon, Higgins & Pendleton, P.A.

(57) ABSTRACT

The present invention provides a phosphonate based compound (B) and a flame resistant thermoplastic resin composition including a thermoplastic resin (A) and the phosphonate based compound (B).

15 Claims, 2 Drawing Sheets

PHOSPHONATE BASED COMPOUND AND FLAME RETARDANT STYRENIC RESIN COMPOSITION INCLUDING THE SAME

CROSS REFERENCE TO RELATED APPLICATIONS

This application is a continuation-in-part of International Application No. PCT/KR2009/007631, filed Dec. 21, 2009, pending, which designates the U.S., published as WO 2010/076995, and is incorporated herein by reference in its entirety, and claims priority therefrom under 35 USC Section 120. This application also claims priority under 35 USC Section 119 from Korean Patent Application No. 2008-135866, filed Dec. 29, 2008, and Korean Patent Application No. 2009-0104023, filed Oct. 30, 2009, in the Korean Intellectual Property Office, the disclosure of each of which is incorporated herein by reference in its entirety.

FIELD OF THE INVENTION

The present invention relates to novel phosphonate based compound and a flame retardant styrenic resin composition including the same.

BACKGROUND OF THE INVENTION

Styrenic resins which are used for exterior materials of electronic devices can also be used in a variety of engineering applications because of their excellent impact resistance, dimensional stability and high heat resistance. However, styrenic resins can burn easily and do not have fire resistance. Accordingly countries such as the United States, Japan and many European countries have passed laws requiring polymer resins to satisfy flame resistance standards.

A widely used and known method for imparting good flame retardancy to styrenic resin includes adding a halogen-containing compound as a flame retardant to a rubber-modified styrenic resin and adding an antimony-containing compound as a flame retardant aid. Examples of halogen-containing compounds used to impart flame retardancy include polybromodiphenyl ether, tetrabromobisphenol-A, epoxy compounds substituted with bromine, chlorinated polyethylene, and the like. Antimony trioxide or antimony pentaoxide is commonly used as an antimony-containing compound.

When a halogen- and antimony-containing compound is used to improve flame retardancy of resins, a desired degree of flame retardancy can readily be imparted to the resulting products without significantly degrading the physical properties thereof. Therefore, the halogen- and antimony-containing compounds are widely used as the primary flame retardant for housing materials for electrical appliances and office equipment formed of ABS resins, PS resins, PBT resins, PET resins or epoxy resins. However, hydrogen halide gases released by halogen-containing compounds during processing can have fatal effects on the human body and have high environmental persistence because these compounds are not naturally degradable. Also these compounds are not soluble in water, and thus can be highly bioaccumulated. Particularly, polybromodiphenyl ether, which is widely used as a halogen-containing flame retardant, may produce toxic gases such as dioxin or furan during combustion, and is consequently harmful to humans and the environment. Accordingly, there is a need to develop flame retardancy methods that do not employ halogen-containing compounds.

SUMMARY OF THE INVENTION

The present invention provides a novel phosphonate based compound which can be added to a resin composition to provide flame resistance.

The present invention further provides a flame resistant thermoplastic resin composition including a novel phosphonate based compound which can have fire stability.

The present invention further provides an environmentally-friendly thermoplastic resin composition which includes a halogen-free flame retardant and which can have excellent flame resistance as compared to a composition including a phosphate ester flame retardant.

Other aspects and advantages of this invention will be apparent from the ensuing disclosure and appended claims.

The present invention provides a phosphonate based compound represented by the following Chemical Formula 1.

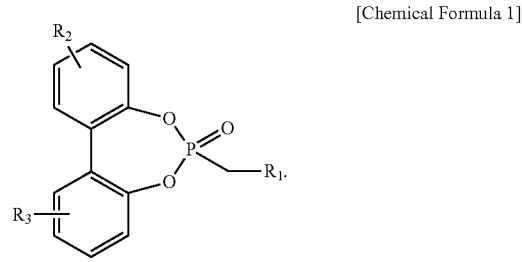

[Chemical Formula 1]

wherein in the above Chemical Formula 1:
R1 is C1 to C4 alkyl, phenyl or cyano, and each R2 and R3 is independently H or C1 to C4 alkyl, for example t-butyl.

The present invention further provides a flame resistant thermoplastic resin composition comprising: a thermoplastic resin (A), and a phosphonate based compound (B) represented by the above Chemical Formula 1.

The thermoplastic resin may comprise polystyrene resin (PS resin), acrylonitrile-butadiene-styrene copolymer resin (ABS resin), rubber modified polystyrene resin (HIPS), acrylonitrile-styrene-acrylate copolymer resin (ASA resin), acrylonitrile-styrene copolymer resin (SAN resin), methylmethacrylate-butadiene-styrene copolymer resin (MBS resin), acrylonitrile-ethylacrylate-styrene copolymer resin (AES resin), polycarbonate resin (PC), poly phenylene ether resin (PPE), polyethylene resin (PE), polypropylene resin (PP), polyethylene terephthalate (PET), polybutylene terephthalate (PBT), polyvinyl chloride (PVC), polymethyl methacrylate (PMMA), polyamide resin (PA), or a combination thereof.

In an exemplary embodiment of the present invention, the flame resistant thermoplastic resin composition may comprise about 100 parts by weight of the thermoplastic resin (A), and about 0.5 to about 30 parts by weight of the phosphonate based compound (B) represented by the above Chemical Formula 1, based on about 100 parts by weight of the thermoplastic resin (A).

In an exemplary embodiment of the present invention, the flame resistant thermoplastic resin composition may further comprise about 1 to about 20 parts by weight of a phosphorus flame retardant (C), based on about 100 parts by weight of the thermoplastic resin (A). The phosphorus flame retardant (C) may be an aromatic phosphorus ester compound (C)-1, a metal salt compound of an alkyl phosphonic acid (C)-2 which has a particle size of less than about 10 μm, or a combination thereof.

DETAILED DESCRIPTION OF THE INVENTION

Figure 1:
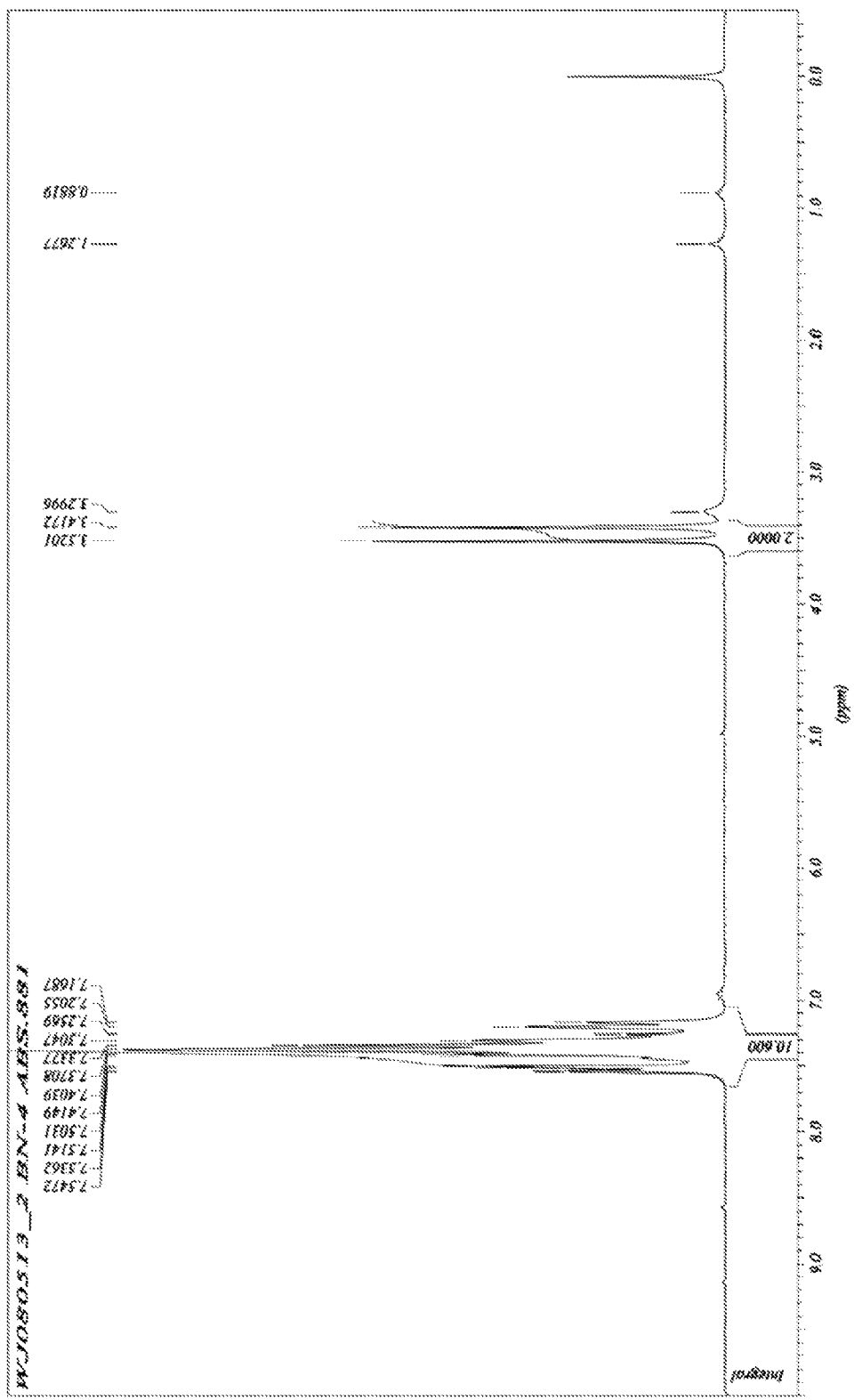
FIG. 1 is a schematic diagram representing the results of 1H-NMR analysis of dibenzo<d,f>[1,3,2]dioxaphos-phepin, 6-phenylmethyl-, 6-oxide according to an exemplary embodiment of the present invention.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

In one exemplary embodiment of the present invention, the present invention provides a phosphonate based compound represented by the following Chemical Formula 1.

[Chemical Formula 1]

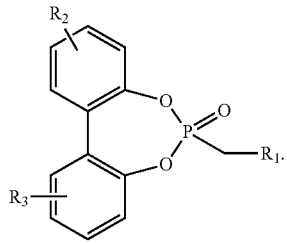

wherein in the above Chemical Formula 1:

R1 is C1 to C4 alkyl, phenyl or cyano, and each R2 and R3 is independently H or C1 to C4 alkyl, for example t-butyl.

For example, the phosphonate based compound represented by the Chemical Formula 1 may comprise dibenzo<d,f>[1,3,2]dioxaphos-phepin, 6-phenylmethyl-, 6-oxide, dibenzo<d,f>[1,3,2]dioxaphos-phepin, 6-cyanomethyl-, 6-oxide, or a combination thereof.

The phosphonate based compound represented by the Chemical Formula 1 can be synthesized according to Scheme 1.

[Scheme 1]

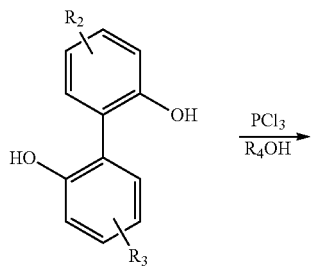

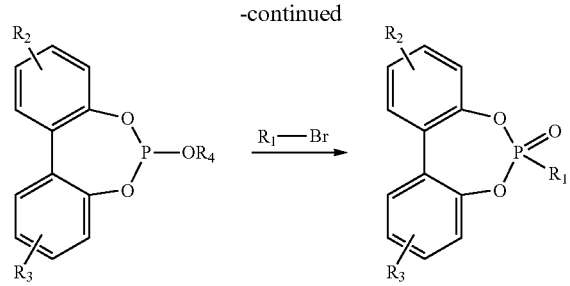

wherein in the above Scheme 1, R4 is C1 to C4 alkyl, and R1, R2 and R3 is the same as described above.

The compound represented by the Chemical Formula 1 according to the present invention can be prepared by preparing an intermediate which is prepared by a dechlorination reaction of phosphorus trichloride, aryl-alcohol and C1-C4 alkanol, such as ethanol, and reacting the intermediate and a benzylbromide or a bromo acetonitrile or a bromo C1-C4 alkane.

Preparations of dibenzo<d,f>[1,3,2]dioxaphos-phepin, 6-phenylmethyl-, 6-oxide and dibenzo<d,f>[1,3,2]dioxaphos-phepin, 6-cyanomethyl-, 6-oxide are described below.

The dibenzo<d,f>[1,3,2]dioxaphos-phepin, 6-phenylmethyl-, 6-oxide and dibenzo<d,f>[1,3,2]dioxaphos-phepin, 6-cyanomethyl-, 6-oxide may prepared as follows. An intermediate such as dibenzo<d,f>[1,3,2]dioxaphos-phepin, 6-C1-C4alkoxy (such as dibenzo<d,f>[1,3,2]dioxaphos-phepin, 6-ethoxy) as illustrated in the Scheme 1 above can be prepared by stirring about 1 to about 3 equivalence ratio of phosphorus trichloride, for example 1 equivalence ratio, about 1 equivalence ratio of 2,2'-dihydroxy biphenyl and about 1 equivalence ratio of C1-C4 alkanol, for example ethanol, in the presence of nitrogen at room temperature. Then about 1 to about 2 equivalence ratio of benzylbromide or bromo acetonitrile or bromo C1-C4 alkane, for example 1 equivalence ratio, is added to the resultant intermediate and the mixture is stirred at about 100 to about 150° C.

In another exemplary embodiment of the present invention, the present invention provides a flame resistant thermoplastic resin composition comprising a thermoplastic resin (A) and a phosphonate based compound (B) represented by the Chemical Formula 1. The phosphonate based compound (B) represented by the Chemical Formula 1 can provide good flame retardancy properties to the thermoplastic resin.

The flame resistant thermoplastic resin composition may comprise about 0.5 to about 30 parts by weight, for example about 5 to about 25 parts by weight, of the phosphonate based compound (B) represented by the Chemical Formula 1 based on about 100 parts by weight of the thermoplastic resin (A). In some embodiments, the flame resistant thermoplastic resin composition may include the phosphonate based compound (B) represented by Chemical Formula 1 in an amount of about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments of the present invention, the amount of the phosphonate based compound (B) represented by Chemical Formula 1 can be in a range from about any of the foregoing amounts to about any other of the foregoing amounts.

If the amount of the phosphonate based compound (B) represented by the Chemical Formula 1 is less than about 0.5 parts by weight based on about 100 parts by weight of the thermoplastic resin (A), flame resistance of the thermoplastic resin composition may be reduced. If the amount of the phosphonate based compound (B) represented by the Chemical Formula 1 is more than 30 parts by weight based on about 100 parts by weight of the thermoplastic resin (A), physical properties of the resin may be reduced.

Examples of the thermoplastic resin may include without limitation styrenic resins (resins including styrene), such as polystyrene resin (PS resin), acrylonitrile-butadiene-styrene copolymer resin (ABS resin), rubber modified polystyrene resin (HIPS), acrylonitrile-styrene-acrylate copolymer resin (ASA resin), acrylonitrile-styrene copolymer resin (SAN resin), methylmethacrylate-butadiene-styrene copolymer resin (MBS resin), acrylonitrile-ethylacrylate-styrene copolymer resin (AES resin), and the like, polycarbonate resins (PC), polyphenylene ether resins (PPE), polyolefin resins, such as polyethylene resin (PE), polypropylene resin (PP), and the like, polyester resins such as polyethylene terephthalate (PET), polybutylene terephthalate (PBT), and the like, polyvinyl chloride (PVC), acrylic resins such as polymethyl methacrylate (PMMA), polyamide resins (PA) and the like, and copolymers and combinations thereof. Accordingly, the resins can include a homopolymer, a copolymer, an alloy and/or a combination thereof.

In one exemplary embodiment of the present invention, the present invention provides a flame resistant thermoplastic resin composition comprising a styrenic resin (A-1), a polyphenylene ether resin (A-2) and a phosphonate based compound (B) represented by the Chemical Formula 1. For example, the flame resistant thermoplastic resin composition may include about 0.5 to about 30 parts by weight of the phosphonate based compound (B) represented by the Chemical Formula 1 based on about 100 parts by weight of a base resin including about 70 to about 99% by weight of the styrenic resin (A-1) and about 1 to about 30% by weight of the polyphenylene ether resin (A-2). As another example, the base resin may include about 15 to about 30% by weight of the polyphenylene ether resin (A-2).

In some embodiments, the base resin can include the styrenic resin (A-1) in an amount of about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent by weight. Further, according to some embodiments of the present invention, the amount of the styrenic resin (A-1) can be in a range from about any of the foregoing amounts to about any other of the foregoing amounts.

In some embodiments, the base resin can include the polyphenylene ether resin (A-2) in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 percent by weight. Further, according to some embodiments of the present invention, the amount of the polyphenylene ether resin (A-2) can be in a range from about any of the foregoing amounts to about any other of the foregoing amounts.

If the amount of the polyphenylene ether resin (A-2) is less than about 1% by weight, the flame resistance of the thermoplastic resin composition may be reduced. If the amount of the polyphenylene ether resin (A-2) is more than about 30% by weight, moldability may be reduced.

The flame resistant thermoplastic resin composition may further comprise a phosphorus flame retardant (C). The phosphorus flame retardant (C) may be an aromatic phosphorus ester compound (C)-1 or a metal salt compound of an alkyl phosphonic acid (C)-2 which has a particle size less than about 10 μm, or a combination thereof.

The phosphorus flame retardant (C) may be used in an amount of about 1 to about 20 parts by weight, based on about 100 parts by weight of the thermoplastic resin (A). In some embodiments, the flame resistant resin composition may include the phosphorus flame retardant (C) in an amount of about 1, 2, 3, 4, 5, 6, 7, 8, 9, 10, 11, 12, 13, 14, 15, 16, 17, 18, 19, or 20 parts by weight. Further, according to some embodiments of the present invention, the amount of the phosphorus flame retardant (C) can be in a range from about any of the foregoing amounts to about any other of the foregoing amounts.

When the flame resistant thermoplastic resin composition according to the present invention further comprises the phosphorus flame retardant (C), the phosphonate based compound (B) may be used in amount of about 1 to about 10 parts by weight, based on about 100 parts by weight of the thermoplastic resin (A).

The aromatic phosphorus ester compound (C)-1 may be represented by the following Chemical Formula 2.

[Chemical Formula 2]

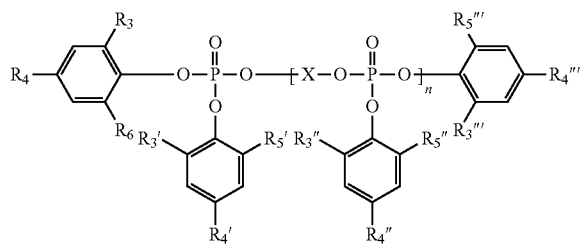

wherein each R3, R4, R5, R3', R4', R5', R3'', R4'', R5'', R3''', R4''' and R5''' is independently H or C1 to C4 alkyl, X is C6 to C20 aryl or C6 to C20 aryl substituted with C1 to C4 alkyl, and n is an integer ranging from 0 to 4.

For example, X may be resorcinol, hydroquinol or dialcohol derived from bisphenol-A, or a combination thereof.

When n is 0, examples of the compound represented by the Chemical Formula 2 may include triphenyl phosphate, tri(2,6-dimethyl)phosphate and the like, and combinations thereof. When n is 2, examples of the compound represented by the Chemical Formula 2 may include resorcinol bis(diphenyl) phosphate, resorcinol bis(2,6-dimethylphenyl)phosphate, resorcinol bis(2,4-ditert-butylphenyl)phosphate, hydroquinol bis(2,6-dimethylphenyl)phosphate, hydroquinol bis (2,4-ditert-butylphenyl)phosphate and the like, and combinations thereof.

The metal salt compound of an alkyl phosphonic acid (C)-2 may be represented by the following Chemical Formula 3, and can have a particle size of less than about 10 μm, for example, about 1 to about 10 μm.

[Chemical Formula 3]

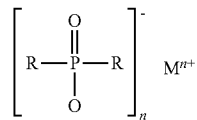

wherein R is C1 to C6 alkyl, C1 to C6 cycloalkyl or C6 to C10 aryl, M is a metal such as Al, Zn, Ca, and n is an integer of 2 or 3.

For example, R may be methyl, ethyl, propyl, butyl or phenyl, and M may be Al or Zn.

The flame resistant thermoplastic resin composition according to the present invention may further include one or more additives selected without limitation from plasticizers, heat stabilizers, antioxidants, compatibilizers, light-stabilizers, inorganic additives, pigments, dyes and the like, and combinations thereof. Examples of the inorganic additives may include asbestos, glass fiber, talc, ceramic, sulfate and the like, and combinations thereof. The one or more additives may be used in an amount of less than about 30 parts by weight based on the total weight of the resin composition.

The flame resistant thermoplastic resin composition of the present invention can be prepared by known methods. For example, the components and optionally the additives can be mixed simultaneously, and the mixture can be extruded through an extruder to prepare pellets.

In another embodiment of the present invention, the present invention provides a molded article prepared from the flame resistant thermoplastic resin composition of the present invention. The molded article may have excellent flame resistance and can be environmentally-friendly. The molded article can be prepared using any suitable molding technique, such as but not limited to melt extrusion, injection molding, and the like. The skilled artisan will understand how to prepare a molded article using the flame resistant thermoplastic resin composition of the invention without undue experimentation.

The invention may be better understood by reference to the following examples which are intended for the purpose of illustration and are not to be construed as in any way limiting the scope of the present invention, which is defined in the claims appended hereto.

EXAMPLES AND COMPARATIVE EXAMPLES

Components used in the following examples and comparative examples are as follows.

(A-1) Styrenic resin: Rubber-reinforced styrenic resin made by Cheil Industries, Inc. of South Korea (product name: HG-1760S) is used.

(A-2) Polyphenylene ether (PPE) resin: Poly(2,6-dimethyl-phenylether) made by Mitsubishi Engineering Plastic Corporation of Japan (product name: PX-100F) is used, and the particle size is several tens of μms in the form of a powder.

(A-3) PET resin: PET resin made by SK Chemical of South Korea (BB-8055) is used, with an intrinsic viscosity [η] of about 0.8, and a melting point of 254° C.

(A-4) ABS resin: ABS resin made by Cheil Industries, Inc. of South Korea (product name: SD-0150) is used.

(B) Phosphonate based compound (B) represented by the Chemical Formula 1: dibenzo<d,f>[1,3,2]dioxaphos-phepin, 6-phenylmethyl-, 6-oxide prepared in Preparation Example 1 and dibenzo<d,f>[1,3,2]dioxaphos-phepin, 6-cyanomethyl-, 6-oxide prepared in Preparation Example 2 are used.

(C)-1 aromatic phosphorus ester compound (C)-1: Bis (dimethylphenyl)phosphate bis-phenol A made by DAIHACHI Chemical Industry Co., Ltd. (product name: CR741S) is used.

(C)-2 metal salt compound of alkyl phosphonic acid (C)-2: Aluminum salt of diethyl phosphonic acid made by Clariant Corporation (product name: Exolit OP930) is used.

Preparation Example 1

Preparation of dibenzo<d,f>[1,3,2]dioxaphos-phepin, 6-phenylmethyl-, 6-oxide: After injecting phosphorus trichloride (137.3 g, 1.0 mol), 2,2'-dihydroxy biphenyl (186.2 g, 1 mol) and ethanol (46.1 g, 1.0 mol) into a receptacle, the mixture is stirred for 3 hours in the presence of nitrogen at room temperature. After adding benzyl bromide (171.0 g, 1 mol), the temperature of the receptacle is raised to 150° C. and the mixture is stirred for 12 hours in the presence of nitrogen. Then, the temperature of the receptacle is lowered to room temperature and the contents are washed with dimethyl ether, and dibenzo<d,f>[1,3,2]dioxaphos-phepin, 6-phenylmethyl-, 6-oxide which has a degree of purity of more than about 98% and a yield rate of about 95% is recovered. FIG. 1 represents the results of 1H-NMR analysis of dibenzo<d,f>[1,3,2]dioxaphos-phepin, 6-phenylmethyl-, 6-oxide prepared by the above method.

Preparation Example 2

Figure 2:
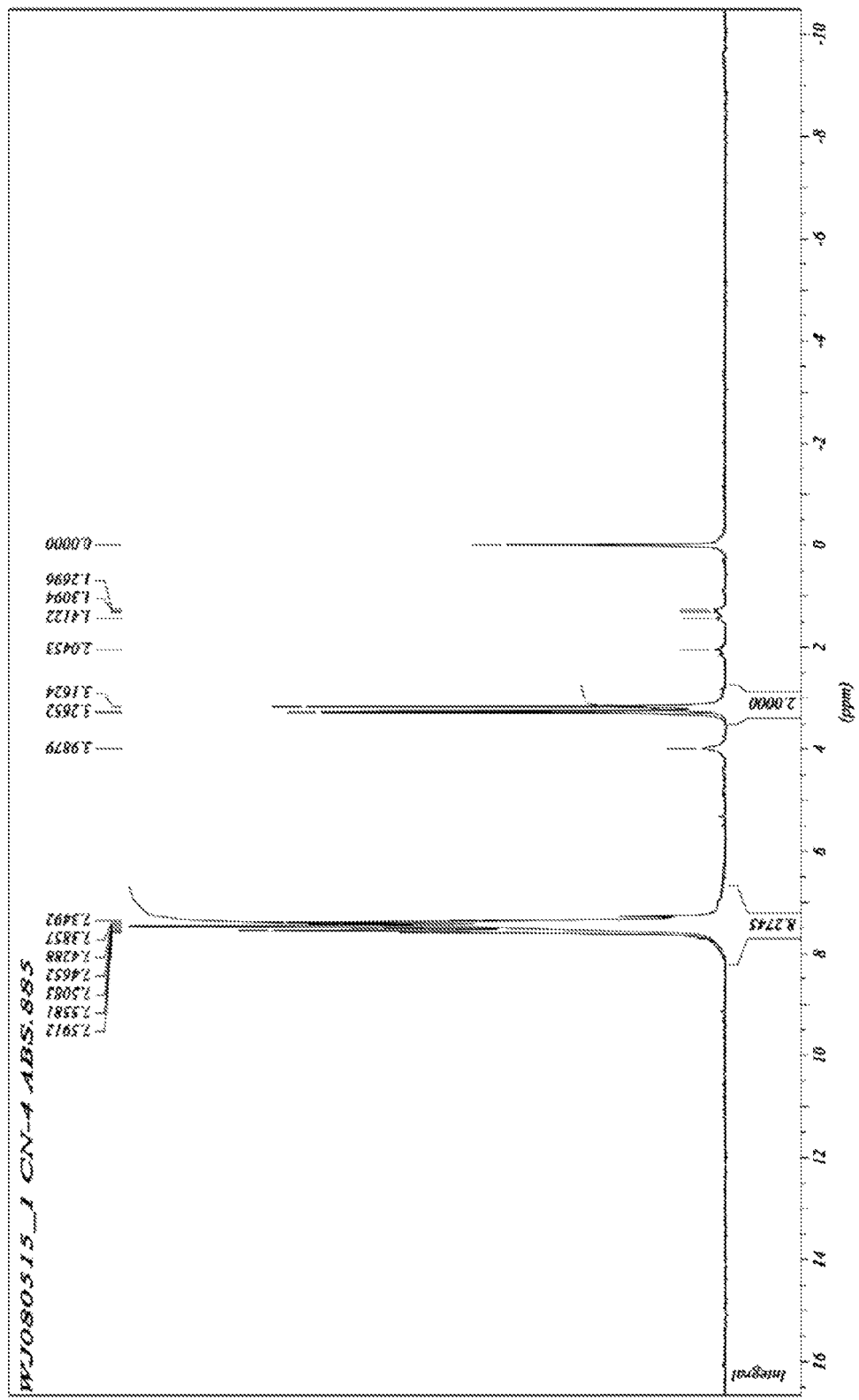
FIG. 2 is a schematic diagram representing the results of 1H-NMR analysis of dibenzo<d,f>[1,3,2]dioxaphos-phepin, 6-cyanomethyl-, 6-oxide according to another exemplary embodiment of the present invention.

Preparation of dibenzo<d,f>[1,3,2]dioxaphos-phepin, 6-cyanomethyl-, 6-oxide: After injecting phosphorus trichloride (137.3 g, 1.0 mol), 2,2'-dihydroxy biphenyl (186.2 g, 1 mol) and ethanol (46.1 g, 1.0 mol) into a receptacle, the mixture is stirred for 3 hours in the presence of nitrogen at room temperature. After adding bromo-acetonitrile (119.9 g, 1 mol), the temperature of the receptacle is raised to 150° C. and the mixture is stirred for 12 hours in the presence of nitrogen. Then, the temperature of the receptacle is lowered to room temperature and the contents are washed with dimethyl ether, and dibenzo<d,f>[1,3,2]dioxaphos-phepin, 6-cyanomethyl-, 6-oxide which has a degree of purity of more than about 98% and a yield rate of about 95% is recovered. FIG. 2 represents the results of 1H-NMR analysis of dibenzo<d,f>[1,3,2]dioxaphos-phepin, 6-cyanomethyl-, 6-oxide prepared by above method.

Examples 1 to 12

The components in amounts shown in the following Table 1 are extruded through a conventional extruder at about 240° C. to prepare pellets. After the prepared pellets are dried, the pellets are injected under conditions of a molding temperature of 230° C. and a tool temperature of 50° C. Then, flame resistant samples are prepared. The flame resistance of prepared samples is measured according to UL 94 VB with a thickness of ⅛" and the impact strength is measured according to ASTM D256.

Comparative Examples 1 to 8

Comparative Examples are prepared in the same manner as the Examples above except the Comparative Examples include the components in the amounts shown in the following Table 2. The results are shown in the following Table 2.

TABLE 1

|  | Examples | | | | | | | | | | | |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| (A-1) HIPS | 85 | 85 | 85 | 75 | 75 | 75 | 75 | 75 | — | — | — | — |
| (A-2) PPE | 15 | 15 | 15 | 25 | 25 | 25 | 25 | 25 | — | — | — | — |
| (A-3) PET |  |  |  |  |  |  |  |  | 100 | 100 |  |  |

TABLE 1-continued

| | Examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| (A-4) ABS | | | | | | | | | | | 100 | 100 |
| (B) Dibenzo<d,f>[1,3,2]di-oxaphosphepin, 6-phenyl-methyl-, 6-oxide | 20 | 15 | — | — | — | — | 15 | — | 15 | — | 25 | — |
| Dibenzo<d,f>[1,3,2]di-oxaphosphepin, 6-cyano-methyl-, 6-oxide | — | — | 15 | 5 | 10 | 20 | — | 15 | — | 15 | — | 25 |
| (C)-1 Aromatic phosphorus ester | — | — | — | 15 | — | — | — | — | — | — | — | — |
| (C)-2 metal salt of alkyl phosphonic acid | — | 5 | 5 | — | — | — | 5 | 5 | — | — | — | — |
| UL 94 flame resistances (1/8") | V-1 | V-1 | V-1 | V-1 | V-1 | V-1 | V-1 | V-1 | V-0 | V-0 | V-0 | V-0 |
| Total burning time | 206 | 165 | 170 | 43 | 120 | 64 | 80 | 82 | 30 | 27 | 42 | 40 |
| IZOD | 3.4 | 5.8 | 5.7 | 4.7 | 5.3 | 4.8 | 6.3 | 6.2 | 6.1 | 5.9 | 6.2 | 6.3 |

TABLE 2

| | Comparative Examples | | | | | | | |
|---|---|---|---|---|---|---|---|---|
| | 1 | 2 | 3 | 4 | 5 | 6 | 7 | 8 |
| (A-1) HIPS | 85 | 85 | 85 | 75 | 75 | 75 | — | — |
| (A-2) PPE | 15 | 15 | 15 | 25 | 25 | 25 | — | — |
| (A-3) PET | | | | | | | 100 | — |
| (A-4) ABS | | | | | | | — | 100 |
| (B) Dibenzo<d,f>[1,3,2]di-oxaphosphepin, 6-phenyl-methyl-, 6-oxide | — | — | — | — | — | — | — | — |
| Dibenzo<d,f>[1,3,2]di-oxaphosphepin, 6-cyano-methyl-, 6-oxide | — | — | — | — | — | — | — | — |
| (C)-1 Aromatic phosphorus ester | 15 | 10 | 20 | 15 | 10 | 20 | 20 | 30 |
| (C)-2 metal salt of alkyl phosphonic acid | 5 | — | — | 5 | — | — | — | — |
| UL 94 flame resistances (1/8") | fail | fail | fail | V-1 | fail | V-1 | V-0 | Fail |
| Total burning time | — | — | — | 103 | — | 120 | 49 | — |
| IZOD | 2.9 | 4.0 | 3.8 | 3.4 | 4.5 | 4.7 | 4.6 | 6.0 |

As illustrated by the results set forth in Tables 1 and 2, when the dibenzo<d,f>[1,3,2]dioxaphos-phepin, 6-phenylmethyl-, 6-oxide and dibenzo<d,f>[1,3,2]dioxaphos-phepin, 6-cyanomethyl-, 6-oxide are used, flame resistance and impact strength are excellent compared to an aromatic phosphorus ester compound.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A phosphonate based compound represented by the following Chemical Formula 1:

[Chemical Formula 1]

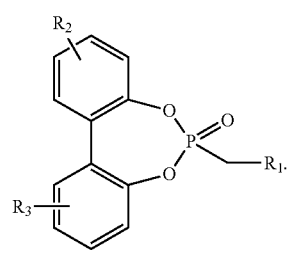

wherein $R_1$ is phenyl or cyano, and each $R_2$ and $R_3$ is independently H or C1 to C4 alkyl.

2. The phosphonate based compound of claim 1, wherein the compound is dibenzo<d,f>[1,3,2]dioxaphos-phepin, 6-cyanomethyl-, 6-oxide.

3. A phosphonate based compound dibenzo<d,f>[1,3,2]dioxaphos-phepin, 6-phenylmethyl-, 6-oxide.

4. A flame resistant thermoplastic resin composition comprising a thermoplastic resin (A) and a phosphonate based compound (B) represented by the Chemical Formula 1.

[Chemical Formula 1]

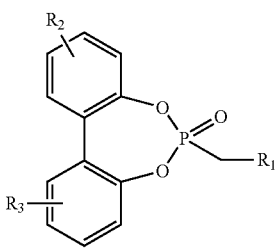

wherein $R_1$ is C1 to C4 alkyl, phenyl or cyano, and each $R_2$ and $R_3$ is independently H or C1 to C4 alkyl.

5. The flame resistant thermoplastic resin composition of claim 4, wherein said thermoplastic resin comprises styrenic resin, polycarbonate resin (PC), polyphenylene ether resin (PPE), polyolefin resin, polyester resin, polyvinyl chloride (PVC), acrylic resin, polyamide resin (PA) or a combination thereof.

6. The flame resistant thermoplastic resin composition of claim 5, wherein said thermoplastic resin comprises polystyrene resin (PS resin), acrylonitrile-butadiene-styrene copolymer resin (ABS resin), rubber modified polystyrene resin (HIPS), acrylonitrile-styrene-acrylate copolymer resin (ASA resin), acrylonitrile-styrene copolymer resin (SAN resin), methylmethacrylate-butadiene-styrene copolymer resin (MBS resin), acrylonitrile-ethylacrylate-styrene copolymer resin (AES resin), polycarbonate resin (PC), polyphenylene ether resin (PPE), polyethylene resin (PE), polypropylene resin (PP), polyethylene terephthalate (PET), polybutylene terephthalate (PBT), polyvinyl chloride (PVC), polymethyl methacrylate (PMMA), polyamide resin (PA) or a combination thereof.

7. The flame resistant thermoplastic resin composition of claim 4, comprising about 0.5 to about 30 parts by weight of the phosphonate based compound represented by the Chemical Formula 1 based on about 100 parts by weight of the thermoplastic resin (A).

8. The flame resistant thermoplastic resin composition of claim 7, further comprising less than about 30 parts by weight of a plasticizer, heat stabilizer, antioxidant, compatibilizer, light-stabilizer, inorganic additive, pigment, dye or a combination thereof based on about 100 parts by weight of the thermoplastic resin (A).

9. The flame resistant thermoplastic resin composition of claim 7, further comprising about 1 to about 20 parts by weight of a phosphorus flame retardant (C) based on about 100 parts by weight of the thermoplastic resin (A).

10. The flame resistant thermoplastic resin composition of claim 9, wherein said phosphorus flame retardant (C) comprises an aromatic phosphorus ester compound (C)-1, a metal salt compound of an alkyl phosphonic acid (C)-2 which has a particle size of less than about 10 μm, or a combination thereof.

11. The flame resistant thermoplastic resin composition of claim 10, wherein said aromatic phosphorus ester compound (C)-1 is represented by the following Chemical Formula 2:

[Chemical Formula 2]

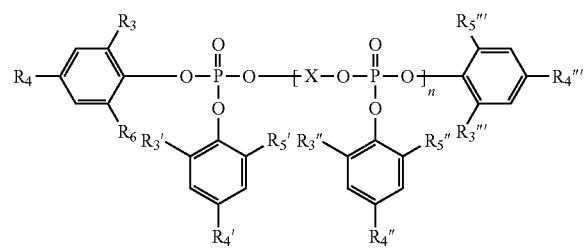

wherein each $R_3$, $R_4$, $R_5$, $R_3'$, $R_4'$, $R_5'$, $R_3''$, $R_4''$, $R_5''$, $R_3'''$, $R_4'''$ and $R_5'''$ is independently H or C1 to C4 alkyl, X is C6 to C20 aryl or C6 to C20 aryl substituted with C1 to C4 alkyl, and n is an integer ranging from 0 to 4.

12. The flame resistant thermoplastic resin composition of claim 10, wherein said metal salt compound of alkyl phosphonic acid (C)-2 is represented by the following Chemical Formula 3:

[Chemical Formula 3]

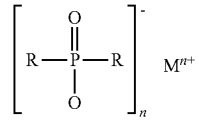

wherein R is C1 to C6 alkyl, C1 to C6 cycloalkyl or C6 to C10 aryl, M is Al, Zn, or Ca, and n is an integer of 2 or 3.

13. A molded article prepared from the flame resistant thermoplastic resin composition of claim 4.

14. The flame resistant thermoplastic resin composition of claim 4, wherein the phosphonate based compound (B) is dibenzo<d,f>[1,3,2]dioxaphos-phepin, 6-phenylmethyl-, 6-oxide.

15. The flame resistant thermoplastic resin composition of claim 4, wherein the phosphonate based compound (B) is dibenzo<d,f>[1,3,2]dioxaphos-phepin, 6-cyanomethyl-, 6-oxide.

* * * * *